United States Patent [19]

Weisz

[11] Patent Number: 5,840,713

[45] Date of Patent: Nov. 24, 1998

[54] THERAPY FOR TISSUE MEMBRANE INSUFFICIENCY

[76] Inventor: Paul B. Weisz, Foxdale Village, Apt. 1-A, 500 E. Marylyn Ave., State College, Pa. 16801-6236

[21] Appl. No.: 530,777

[22] Filed: Sep. 19, 1995

Related U.S. Application Data

[63] Continuation-in-part of Ser. No. 416,107, Apr. 3, 1995, Pat. No. 5,760,015.

[51] Int. Cl.$^6$ .......................... A61K 31/715; C08B 31/16
[52] U.S. Cl. .............................................. 514/58; 536/103
[58] Field of Search ............................... 514/58; 536/103

[56] References Cited

U.S. PATENT DOCUMENTS

| | | | |
|---|---|---|---|
| 5,019,562 | 5/1991 | Folkman et al. | 514/58 |
| 5,093,106 | 3/1992 | Dzbanovsky et al. | 424/7.1 |
| 5,155,810 | 10/1992 | McNamara, Jr. et al. | 395/250 |
| 5,183,809 | 2/1993 | Weisz et al. | 514/58 |
| 5,262,404 | 11/1993 | Weisz et al. | 514/58 |

FOREIGN PATENT DOCUMENTS 0431735  6/1991  European Pat. Off. .

OTHER PUBLICATIONS

Weisz et al, "Angiogenesis and heparin mimics", Angiogenesis–Key Principles, Science, Technology. Med. 1992 pp. 107–116.

Farquhar, "The Glomerular basement Membrane", Cell Biology of Extracellular Matrix., Plenum Press, 1988, pp. 335–378; pp. 335–336 only.

Gambaro et al, Role of glycosoaminoglycans in diabetic nephropathy:, Acta. Diabet. 29, No. 34, 1992, pp. 149–155. Abstract only.

Pukerson et al, "Pathogenesis of the glomerulopathy associated with renal infarction in rats", Kidney Intern. 9, 1976, pp. 407–417. Abstract only.

Mogensen, "Systemic blood pressure and glomerular leakage with particular reference to diabetes and hypertension", J. Int. Med. 235, No. 4, 1994, pp. 297–316. Abstract only.

Yu et al, "Physiologic Modulation of Bronchial Epithelial Cell Barrier Function by Polycationic Exposure", Am. J. Respir. Cells and Molecular Biolog. 11. 1994. 188–198. Abstract only.

Staehelin et al, "Lumenal Plasma Membrane of the Urinary Bladder", J. Cell Biol. 53, 1972, pp. 73–91. Abstract only.

Parsons et al, "Successful treatment of interstitial cystitis with sodium pentosanpolysulfate", J. Urol. 130(1), 51–3, 1983 Jul. Abstract only.

Parsons et al, "Bladder Surface Glycosaminoglycans: An Epithelial Permeability Barrier". J. Urol. 143, Jan. 1990, pp. 139–142r. Abstract only.

Murch et al, "Disruption of sulphated glycosaninoglycans in intestinal inflammation", The Lancet, vol. 341, Mar. 20, 1993, pp. 711–714. Abstract only.

Baum et al, "Angiodysplasia of the Right Colon: A Cause of Gastrointestinal Bleeding", Am.J. Roentgenol 129, No. 1977, pp. 789–794. Abstract only.

Ichikawa et al, "Effect of heparin on the ghlomerular structure and function of remnant nephrons", Kidney Inter. vol. 34, 1988, pp. 638–644. Abstract only.

Gambaro et al, "Glocosaminoglycans prevent morphological renal alterations and albuminuria in diabetic rats", Kidney Interntl. vol. 42, 1992, pp. 285–291. Abstract only.

Thornton et al, "Human Endothelial Cells: Use of Heparin in Cloning and Long–Term Serial Cultivation", Science 222, No. 1983, pp. 623–625. Abstract only Folkman et al, "Angiogenesis Inhibition and Tumor Regression Caused by Heparin or a Heparin Fragment in the Presence of Corisone", Science, 221, 1983, 719. Abstract only.

Crapper et al, "Brain Aluminum Distribution in Alzheimer's Disease and Especially in the Neurofibrillary Tangles", Science 180, May, 1973, pp. 511.

Kare et al, "Direct Pathway to the Brain", Science, vol. 163, No. 1986, p. 952.

Stokes et al. *Microvascular Research* 1990, 40, 279–284.

Frijlink et al. *Pharmaceutical Research* 1991. 8(1), 9–16.

Szejtli "Industrial Applications of Cyclodextrins". In inclusion Compounds, vol. 3, Physical Properties and Applications. J. L. Atwood et al., editions. Academic Press, London, 1984,pp. 331–390

*Primary Examiner*—Kathleen K. Fonda
*Attorney, Agent, or Firm*—Glenn & Hendricks; Stephen Gates

[57] ABSTRACT

Disclosed are methods of therapy applicable to pathologies that involve loss of integrity of tissue and organ membranes that lead to abnormal permeation of proteinic and other agents and their elimination or penetration of other anatomical functions. Such deficiencies are associated directly or indirectly, for example, with inflammatory diseases, with diabetes and others. The therapeutic method involves administering to the membrane in need of treatment a therapeutic amount of an oligosaccharide, preferably a cyclic oligosaccharide, having up to about 10 sugar units per molecule and having at least 1.4 anionic substituents per sugar unit. The anionic substituents are preferably the residues of strong acids.

17 Claims, No Drawings

THERAPY FOR TISSUE MEMBRANE INSUFFICIENCY

This application is a continuation-in-part of U.S. patent application Ser. No. 08/416,107, filed Apr. 3, 1995, now U.S. Pat. No. 5,760,015, the entire contents of which is incorporated herein by reference.

This invention is concerned broadly with therapeutic methodology applicable to pathologies that are due to, or are accompanied by, abnormal leakage of proteinic or other substances through tissue membranes. The invention is more specifically directed to the use of specific substances to reverse the condition of abnormal membrane permeation and to reestablish membrane permeation at a normal state. This invention is also directed to methods of administration of such substances. Although this invention is generally directed to the treatment of all abnormal membrane penetration problems, it is most concerned with the treatment of nephritic, urological, pulmonary, gastric and other diseases which are especially associated with the deteriorating integrity of tissue membranes.

1. BACKGROUND OF THE INVENTION

1.1 Tissue Leakage in Various Pathologies

A large number of disease states are characterized by leakage of an abnormal amount of proteinic components through the tissue membranes that normally provide a barrier to the penetration by, and passage of, these components. Leakage states may progress from allowing a limited degree of small molecules, such as water and small ions, to penetrate through membranes, to the state where the barrier structure has deteriorated to the point of allowing larger molecular entities, including small proteins and larger proteinic substances, and biological agents, to "leak" through membranes (see e.g. J. R. Pappenheimer et al., Filtration, Diffusion and Molecular Sieving Through Peripheral Capillary Membranes, *Am. J. Physiol.* 167, 13–46, 1951; and M. G. Farquhar, The Glomerular Basement Membrane: A Selective Macromolecular Filter. In *Cell Biology of Extracellular Matrix*. 335–378, Plenum Press, 1988).

A most commonly known phenomenon of physiological membranes which are in the process of breaking down is the occurrence of albuminuria, i.e. of leakage of albumin from the glomerular membrane of the kidney into the urine. This phenomenon occurs in advanced stages of diabetes (see e.g. G. Gambaro and B. Baggio, *Acta Diabet*. 29, No. 3/4, 149–155, 1992). It can also result from other nephritic diseases (see e.g. M. L. Purkerson et al., Pathogenesis of the Glomerulopathy Associated with Renal Infarction in Rats, *Kidney Intern*. 9, 407–417, 1976). It also has been noted to accompany chronic hypertensive states (see for example, C. E. Morgensen, Systemic Blood Pressure and Glomerular Leakage with Particular Reference to Diabetes and Hypertension, *J. Int. Med*., 235, No. 4, 297–316, 1994).

It has been shown that, in the lungs, factors released by inflammatory cells can compromise the functional barrier to the leakage of water and solutes therein that is normally maintained by the bronchial epithelial cell membrane located between the luminal and interstitial compartments of the lungs (see X. Y. Yu et al. Am. J. Respir. *Cell & Molecular Biolog*. 11, 188–89F, 1994).

The mammalian bladder also is provided with an epithelial membrane that inhibits water and ionic substances from leaking into the bladder (see e.g. L. A. Staehelin et al., Luminal Plasma Membrane of the Urinary Bladder, *J. Cell Biol*. 53, 73, 1972). Insufficiencies in maintaining this barrier lead to leakage and disease states such as, for example, interstitial cystitis (see e.g. C. L. Parsons et al., Successful Treatment of Interstitial Cystitis with Sodium Pentosanpolysulfate *J. Urol*. 130, 51; and C. L. Parson et al., Bladder Surface Glycosaminoglycans: An Epithelial Permeability Barrier, *J. of Urology*, 143, 139–142r, 1990).

It is becoming increasingly evident that the disruption of the integrity of membranes toward penetration by proteinic substances and other constituents of blood plasma is playing a role in many pathologies. It occurs, for example, in Crohn's disease and other inflammatory diseases of the bowel (see e.g. S. H. Murch et al., *The Lancet*, 341, 711–714, 1993). Similar violations of membrane integrity leading to intermittent leakage of blood components appear to accompany or cause angiodisplasia (see S. Baum Am. J. Roentgenol. 129, 789–794, 1977).

There is evidence that glycosaminoglycans, especially heparin or heparin sulfate proteoglycans, play a role in the maintenance of membrane sufficiency. Heparin itself, exogenously applied, has been shown to improve non-permeability in in vitro and in vivo cellular and tissue studies (see references above, and I. Ichikawa et al., Effect of Heparin on Glomerular Structure and Function of Remnant Nephrons, *Kidney intern*. 34, G38–G44, 1988; G. Gambaro and B. Baggio, *Acta Diab*. 29, 149–155, 1992; G. Gambaro et al., *Kidney Intern*. 42, 285–291, 1992).

In a different field of biomedicine, heparin has been shown to perform functions related to modulating cell proliferation, such as accelerating endothelial cell multiplication (see, for example, S. N. Mueller et al. *J. Cell Physiol*. 149, 439–448F, 1989); or inhibiting smooth muscle cell proliferation and, in combination with certain steroids, it can inhibit endothelial cell growth and angiogenesis (see J. Folkman el al., *Science* 221, 719, 1983).

1.2. Heparin

Heparin is an oligosaccharide, that is a saccharide composed of a long chain of some 25 to 50 linked sugar units. Each of these sugar units has additional substituent groups attached thereto in the place of one or more of the hydroxyl groups of the ordinary saccharide molecule. This more complex structure is referred to as a glycosaminoglycan (GAG) . There are various GLG's known besides heparin, and they are distinguished from each other in specific detail as to structural position, number and type of substituent groups. These substituent groups are O-sulfate, N-sulfate, carboxyl and hydroxy groups. In addition, various of the sugar units in the GAG chain have designated names representing different structural arrangements of the substituents in the sugar units: such as 2,6 disulfo-glucosamine, 2-sulfoiduronate, and beta-glucuronate. Heparin has now been known and used for many decades in medical practice for its unique anticoagulant activity.

1.3. Anionically Substituted Cyclodextrins

Cyclodextrins are also oligosaccharides, in that they consist of a linked glucose units. These compounds are of much lower molecular weight and size than heparin, and consist of only six, seven or eight glucose units, in which case they are referred to as alpha-, beta- and gamma-cyclodextrins, respectively. Thus, their molecular weights are less than the molecular weights of heparin by a large factor. Furthermore, they are cyclic structures, in the form of a doughnut (toroid) shaped ring, wherefore they are called cyclodextrins. Having a cyclic structure also results in the distinction from other sugars, like dextrans and glycosaminoglycans, in that they do not possess any "end groups".

There are three hydroxyl groups associated with each glucose unit in cyclodextrins. A large variety of chemical groups can be substituted in place of, or added to, through ether or ester linkages, some or all of the hydroxyl substituents. It has been demonstrated that when cyclodextrins are provided with a critical number of anionic groups, such as about 1.5 or more sulfate substituents per glucose unit, they possess biological activity for the modulation of cell proliferation which is qualitatively similar to, but often better than, the modulation activity of the heparins (see P. B. Weisz et al. Angiogenesis and Heparin Mimics, in *Angiogenesis-Key Principles-Science-Technology Medicine*; R. Steiner, P. B. Weisz, R. Langer, Ed.s, Birkhauser/Springer 1992). These agents were also found to provide anti-viral protection to human cells and to protect erythrocytes against hemolytic agents. It is interesting that the anionically substituted cyclodextrins do not seem to possess the anticoagulation activity which characterize heparin.

2. Objects of the Invention

It is an object of this invention to provide effective methods of pharmacological therapy for mammals, including humans, that suffer from diseases or disease states characterized by defective tissue membranes resulting in undesired and pathological leakage of proteins or other plasma components through such membranes. Such diseases are generally inflammatory diseases that involve the endothelium, epithelium, basement membranes and other vital tissue surfaces of organs, such as the kidney, the lungs, the bowel, the urinary bladder, and the ureter.

Among the more specific objects of this invention are, inter alia:

1. provision of therapeutic means and methods to inhibit the deterioration of the kidney function, such as in consequence of diabetes, characterized by progressive leakage of albumin and other proteinic substances into the urine;
2. provision of means and methods to alleviate deficiencies in the tissues of the lumen of the bowel, such as in Crohn's and other inflammatory bowel diseases;
3. provision of means and methods to treat inflammatory disease of the bladder, such as interstitial cystitis; and
4. provision of means and methods to treat inflammatory diseases involving the lungs, such as may be induced by allergic or other stimuli.

The anionically substituted cyclooligosaccharide, such as the cyclodextrins, which are used in this invention do not require other types or varieties of compositional or structural chemical group substituents, in addition to those specified herein, to perform the therapeutic functions described herein. This stands in contrast to the heparins that require sophisticated structurally modifying components that provide the anticoagulant activity of the heparin molecule (see C. A. A. van Boeckel and Maurice Petitou, The Unique Antithrombin III Binding Domain of Heparin: Ahead to New Synthetic Antithrombins, *Angew. Chem. Int. Ed. Engl.* 32, 1671–1690f, 1993). In fact, it must be understood that it is a major advantage of the agents in this invention that they do not possess any substantial antithrombin activity. They can be utilized at effective dosage levels for the purposes of this invention at which heparin could not be used because of its anticoagulant activity leading to serious, including possibly lethal, side effects.

The relative chemical and structural simplicity of the agents employed by this invention provides another advantage in utility: they are easily and economically synthesized from available cyclooligosaccharides, such as cyclodextrins. This stands in drastic contrast to the efforts to produce modified synthesis products derived from heparin, or even of low molecular weight heparin fragments, that have been investigated in past years. For example, cyclodextrins are derivatized to bear the desired sulfate, or other anionic, groups desired for use in this invention by directly and easily reacting a cyclodextrin, or other relative small polysaccharide, preferably cyclopolysaccharide, molecules, in an aprotic solvent with a sulfating or sulfonating agent, such as, for example: chlorosulfonic acid, or with sulfur trioxide complexed with either trialkylamine or with pyridine, or the like. These reactions are per se known. This stands in contrast to the numerous steps of chemical synthesis required in past efforts to produce biologically active glycosaminoglycans or derivatives or variants of same.

It is important for the agents of this invention to contain the critical minimum number of the anionic constituents. However, the biological activity provided in this invention does not seem to be sensitive to other structural detail of the agents employed. Thus, many anionic substituted low molecular weight polysaccharides are suited to use in this invention, as represented by the above described cyclodextrins. As long as the average number of anionic molecules lies above a critical average, the exact distribution of the groups on any specific position of the sugar units does not seem to be a critical limitation on the effectiveness of these reagents. Also, other positions on the sugar units may have other substituents, especially groups that are not substantially cationic, such as, for example, alkyl, alkyl-ether or thio-ether, or a variety of other substituent groups. Suitably these substituents are not limited in chain length. However, in the case of alkyl groups, those containing up to about 6 carbon atoms can suitably be used. This stands in contrast to the widely adopted assumption that most, if not all, biologically active molecules are highly sensitive to the specific molecular structure of the active molecule.

While the membrane modifying activities of the cyclodextrins of this invention do not require the employment of one or more added substituent(s), beneficial effects can result from addition of certain other substituents. For example, the addition of hydrophobic or lyophilic substituents on some positions of the sugar units of the low molecular weight anionic substituted polysaccharide of this invention can provide for better surface adhesion of these compounds to the tissue membranes by causing partial penetration of the substituted polysaccharide (cyclodextrin) into cell or tissue surfaces. Such compositional variants that would serve for such purpose are described in U.S. patent application Ser. No. 08/416,107.

2.2 Therapeutic methods

According to this invention, highly anionic cyclodextrin compositions of the nature described above are administered to mammals when a pathology of membrane insufficiency or incipient breakdown is indicated. That is, when it is discovered that certain molecular components are being transmitted through portions of tissue or organs in an abnormal manner or at an abnormal rate, treatment according to this invention is indicated. Also, such agents are usefully administered to prevent development or progressive deterioration of such condition.

The agents of this invention are beneficially employed to treat existing conditions of nephropathies and glomerulopathies, such as glomerulonephritis and glomerulosclerosis, as may be caused or aggravated by toxins, bacterial agents, chronic serum disease, diabetes mellitus, hypertension and various other causes of morphological and functional renal abnormalities. The agents may also be employed as preventatives of the development or progression of such renal pathologies.

Similarly, in accordance with this invention, the agents are administered to mammals, including humans, suffering from inflammatory pathologies of the bowel, thereby restoring the integrity of epithelial membrane and the extracellular matrix, and preventing escape of proteinic and other substances from the plasma into the lumen. The intimate physiological relationship, namely the common basis of tissue membrane leakage in this realm of pathology and the renal pathologies noted above, is well demonstrated by the evidence of hypoalbuminaemia that accompanies chronic bowel disease by way of loss of albumin into the intestinal lumen.

The procedures and agents of this invention are also employed in reducing inflammatory conditions of the epithelial cell membrane of the bladder, such as occurs in interstitial cystitis. Administration of a solution, especially an aqueous solution, or a solution in other physiologically acceptable solvents or carriers, of the agents as described, such as by direct irrigation of the bladder, is indicated particularly in chronic conditions of cystitis.

Evidence has developed for a role of undesired permeation or leakage of substances through or along anatomical membranes as a vulnerable step in the chain of physiological events that can ultimately express Alzheimer's disease. It is widely known that aluminum has consistently been found in abnormally higher concentration in the brain of victims of this disease (see for example, D. R. Crapper et al., Brain Aluminium Distribution in Alzheimer's Disease and Especially in the Neurofibrially Tangles, Science 180, 511–13, 1973); aluminum has been shown to occur associated with silicon in senile plaque, the brain lesion characteristic of the Alzheimer syndrome (see J. M. Candy et al., Aluminosilicates and Senile Plaque Formation in Alzheimer's Disease, Lancet, 1986, 354–357); the association of aluminum with silicon is characteristic of highly catalytically active matter, capable of causing decomposition reactions to occur on contact with many compositions (see W. O. Haag et al. The Active Site of Aluminosilicate Catalysts, Nature 309, 589–591, 1984); clay is a major component of dust, a ubiquitous ingredient of the environment and the air we breathe, and it is an association of aluminum and silicon atoms that can catalyze molecular alterations; and it has been shown that there can occur conditions of leakage of foreign matter, including aluminum containing entities, from the nose to the brain along the olfactory nerve (see M. Are et al., Science 163, 952–953, 1968; D. P. Pal and P. F. Good, Uptake of Aluminum into Central Nervous System Along Nasal-Olfactory Pathways, Lancet, 1987, 1028). It is believed that the administration, to the olfactory system, of agents and methods described in this invention will arrest the leakage of such matter to the brain to prevent development or progression of brain lesions such as are involved in Alzheimer's disease.

The therapeutic methods of the invention are seen to also apply to undesired and abnormal conditions of permeability in other locations of the anatomy, involving tissues, vessels and organs other than those noted above.

It is a further object of this invention to provide effective methods of delivery for the agents of this invention which are capable of regulating membrane sufficiency as stated.

These and other objects, aspects and advantages of the present invention will become apparent to those skilled in the art upon reviewing the following description and appended claims.

3. DESCRIPTION OF THE INVENTION

This invention derives from a study of the biological activities of certain highly anionic polysaccharides of low molecular weight and relatively rigid geometric structure, such as cyclodextrins, wherein a large number of hydroxyl groups, above a critical minimum, have been substituted by anionic groups, such as sulfate groups. Surprisingly, it has been found that the relatively small and chemically simple cyclodextrin sulfates, with the critical minimum number of sulfate substituents, perform a variety of functions which are similar in nature to those that previously have been associated only with the very complex and heterogeneous compositions known as glycosaminoglycans. According to this invention, this capability extends beyond possessing the ability to alter proliferation behavior of individual cell species. According to this invention, these anion substituted cyclodextrins are also capable of altering the properties of cell and tissue membranes so as to restore their ability to prevent undesired and abnormal leakage of proteinic and other substances across such membranes. According to this invention, when they are administered to a mammal, the low molecular weight, anionic substituted polysaccharides, e.g. cyclodextrins, of this invention thereby have beneficial therapeutic capabilities in regard to the treatment of a number of pathologies that specifically involve membrane transfer insufficiencies, particularly such conditions as lead to undesired leakage of proteins or other agents through these tissue membranes.

3.1 The Agents Employed in the Invention

The agents used in this invention are relatively low molecular weight polysaccharides that are polyanionic substituted to the extent of having, on the average, at least about 1.4 anionic substituents per sugar unit. While heparin falls within the general category of polysaccharides having this level of anionic substitution, and has been shown to have some capability to modulate membrane permeability, the polyanionic agents of this invention differ in important structural details, as well as their biological activity from heparin, in that they lack any substantial anticoagulant activity. This allows their effective application for the therapeutic purposes and methods of this invention at dosage levels at which the use of heparin would be counterindicated, if not associated with great risks of internal bleeding, stroke, etc. The compounds being used in the instant invention provide many advantages in application, effectiveness of delivery, reproducibility, stability against degradation and ease of supply.

The agents used in this invention are low molecular weight saccharides, having only about two to ten sugar units compared to some twenty to fifty units in heparin. In a preferred aspect of this invention, the instant used compounds have six to eight sugar units and are cyclic in structure. They therefore have no end groups and thereby contrast to the non-cyclic, open chain structure of heparin. The low molecular weights of the agents employed in this invention thereby allow faster diffusion, distribution and accessibility through body fluids and biological structures than would be the case for heparin, or other high molecular weight polysaccharides, even if such high molecular weight polysaccharides, such as heparin, were otherwise equally effective. The compounds which are used in the practice of this invention preferably have molecular weights of about 1,000 to 4,300, comprising between about 2 and 10 sugar units per polysaccharide molecule, and bear a critical minimum of about 1.4 anionic substituents per sugar unit within each molecule. The low molecular weights of the agents being used in this invention should be compared to molecular weights which range from about 12,000 to 24,000 for heparin molecules. The minimum number of anionic substituents per sugar unit will be about 1.4 for saccharides of about 6 to 10 sugar units, including the preferred cyclic saccharides of this invention, the cyclodextrins. The critical minimum ratio will be even greater for smaller saccharides. For example, for trisaccharides, the minimum number of anions will be about 2.5; and for disaccharides, the minimum number of anions will be about 3.5 per sugar unit. Sucrose octasulfate, for example, has a ratio of anions per sugar unit of 4.

The preferred agents for use in this invention are the cyclic saccharides: alpha, beta and gamma-cyclodextrin, having 6, 7 and 8, sugar units respectively. The most preferred agent for use in this invention is beta-cyclodextrin. The anionic substituents are the physiologically acceptable residues of strong acids, such as sulfates, phosphates, sulfonates, and phosphonates. The preferred anionic groups are the sulfates and the phosphates, with the sulfates being the most preferred for the practice of this invention.

While the agents utilized in this invention are characterized by the structural features described above, the term "sugar unit" is to be understood to apply broadly to isomeric variants, and may include: inter alla, hexose and/or pentose sugar units as part or all of the polysaccharide agents being used in this invention. Within the context of the molecular weight and anion concentration limits set forth above, and provides there is biological acceptability, other components may be added to the active agents of this invention, and/or other substituents may be substituted on the sugar units. These additional substituents may have various effects including therapeutic or physical effects, in that they may regulate solubility and compatibility as needed. Where additives are included with, or substituted on, the anionically substituted polysaccharides of this invention, the molecular weights of the active ingredients should be calculated without consideration of the molecular weights of these other substituents.

This invention involves the administration of the agents described, or combinations of such agents, including their combination with other pharmaceutically desirable components or molecules, in a physiologically acceptable vehicle, such as water. The mode of administration and the choice of concentration of the specific cyclic polysaccharide agent of this invention will depend on the anatomical target intended to be reached, the condition of the recipient and the other usual medical considerations for optimizing effectiveness and minimizing risk of untoward effects. Generally, the administration would involve oral, topical or parenteral, e.g., intravenous or subcutaneous, delivery.

It is contemplated that the active agents in this invention will be administered at a dosage of between about 0.1 to 10 milligrams per day/kg of body weight, if administered parenterally. Comparable doses can be otherwise administered. This dosage may be given at one time or in smaller multiple aliquots. However, when the anionic cyclodextrins of this invention also bear substantial hydrophobic (lipophilic) substituents, the required dosage may possibly be able to be lowered depending on the nature and degree of hydrophobicity of the agent. Daily dosage will therefore be whatever is significantly helpful to the patient, but will preferably range up to about 0.1 to 1.0 mg/day/kg.

Similar daily dosage quantities are delivered in the case of pulmonary delivery, whereby the agents may be suitably contained in an aqueous or vaporous carrier solution that is delivered by a misting or spraying device into the air breathed or inhaled by the recipient. This methodology is considered to be an alternative to oral delivery when choosing a non-parenteral mode of delivery; however, it is seen as particularly advantageous when the pulmonary system itself is involved as a therapeutic target, such as in the case of allergic and asthmatic conditions and to inhibit histamine release responses. In some cases, when the target of treatment is the pulmonary system itself and direct application of the medicament is possible, dosage requirements may be found to be below 1.0 mg/day/kg of body weight, preferably about 0.01 to 1.0 mg/day/kg of body weight.

Oral administration will be particularly preferred in the case of targeting urinary or gastrointestinal conditions. On the other hand, in the case of diseases of the bladder or intestines, the procedures of topical application by direct irrigation by infusion of fluids bearing the agent and temporary retention will be advantageous. The irrigating fluids in such case would suitably be solutions of about 0.1 to 10 mg/ml of the active agent of this invention.

Other modes and variants and combinations of modes may be employed for the practice of the therapies of this invention. For example, the agents may be encapsulated in suitable release vehicles, porous materials, or bio-erodible materials, or adsorbed on porous sorbents, after which such materials are administered to appropriate locations for subsequent emission to tissues, or organs of the body. Among other methods of delivery are the use of transdermal methods such as electroporation aided delivery. Also, the agents, being highly anionic compositions, may be contacted with cationic materials to form salts which have finite dissociation capabilities, so as to be capable of re-dissociating slowly after delivery. Such complexing partners include physiologically acceptable inorganic cations, such as calcium or magnesium, or cationic compounds including amino acids, such as lysine, polyaminoacids, such as polylysine, and other peptides that comprise one or more amino-acids from the list of lysine, arginine, and/or histidine, or various diamines or tertiary amino compounds.

EXAMPLES

The following examples shall illustrate the invention. They are not to be construed to be limiting the scope of the invention, inasmuch as the scope shall be determined by the appended claims.

Example 1

Preparation of polysulfated beta-cyclodextrin

Chlorosulfonic acid (7.5 ml) was added dropwise to pyridine cooled to −10° C. The resulting solid was warmed to 58° C. and beta-cyclodextrin powder added in small portions (1.7 g total) and stirred for 72 hours. The product was stirred into 1 liter of methanol, subsequently filtered from the methanol and dissolved in 80 ml of 10% aqueous sodium acetate. The solution was washed with 40 ml of toluene. 1 Gram of charcoal was added and the filtered solution was precipitated, by adding 70 ml of ethanol, to yield the polysulfated cyclodextrin product.

Example 2

Purification and analysis of Polysulfated beta-cyclodextrin

The polysulfated beta-cyclodextrin product from Example 1 was examined by elemental analysis and for uniformity by Sephadex (60 g) chromatography with water as eluant. 95% of the product (discarding the lightest fraction of eluent) contained 16.3 wt. % of sulfur, corresponding to 12.3 sulphate groups per molecule of cyclodextrin.

Example 3
Bioloaical activity of polysulfated cyclodextrin

The polysulfated cyclodextrin obtained by examples 1 and 2 were tested for biological activity, which in previous work had been found to require a minimum of about 10 sulfate groups per molecule. An in vitro procedure was employed to observe the agent's ability to inhibit the proliferation of human umbilical vein smooth muscle cells. A coating of cells were allowed to attach to fibronectin coated plates and incubated with varying concentrations of the cyclodextrin polysulfate sample and 10% of calf serum. Cells were fixed, stained with naphtha blue-black, lysed, and quantitated by light absorptivity at 530 nm. 50% Inhibition of cell proliferation was achieved at 1.0 t 0.2 mg/ml of agent for several fractions of the 95% portion of purified agent from example 2.

Example 4
Reduction of albuminuria

As an animal model for diabetes, rats are given i.v. streptozotocin, such as 50 mg per day/kg, diabetes and its characteristic symptoms can be observed after four weeks, and the daily urinary output of albumin reaches about 500 micrograms; see the study of Y. Oshima et al., Diabetes Research & Clinical Practice 25, 83–89, 1994. Subsequent daily injection s.c. of polysulfated cyclodextrin agent markedly reduces albuminuria. While heparin delivery also has such beneficial effect, the polysulfated cyclodextrin is effective at a lower daily dosage, or upon delivery at longer intervals between treatments.

Example 5
Albumin leakaae through endothelial cell layer

When a layer of endothelial cells is deposited on a membrane with pores smaller than the cell dimensions, the ability of ions, such as sodium or of proteins, such as albumin, to penetrate, and flux rate of penetration, can be observed. When one side of this cellular membrane is exposed to polycationic proteins such as prolamine, a discernable increase of penetration by albumin through the membrane results. Subsequent exposure of the surface to the polyanionic cyclodextrin of Example 2 results in a marked restoration of membrane sufficiency as shown by a decrease of albumin penetration through the membrane.

Example 6
Albumin leakaae throuah epithelial cell layer

A similar behavior as in example 5 is exhibited when a layer of epithelial cells is exposed to damaging agents as in Example 5. The effectiveness of the epithelial cells is restored by subsequent treatment with the agents of this invention.

What is claimed is:

1. A therapeutic method for reducing pathologically excessive permeability of tissue membranes of a mammal to leakage of proteinic substances therethrough, which method comprises administering, to a mammal exhibiting effects of tissue membrane leakage, an oligosaccharide selected from the group consisting of α-, β-, and γ- cyclodextrins which is substituted with at least about 1.4 anionic groups selected from the group consisting of sulfate, phosphate or sulfonate per sugar unit, in an amount which is effective to reduce leakage of proteinic substances through said membrane.

2. The method of claim 1 wherein the anionic groups comprise sulfates.

3. The method of claim 1 wherein said membrane comprises an insufficiently functioning glomerular membrane of the kidney resulting in urinary excretion of albumin, and wherein said oligosaccharide is administered in sufficient quantity and frequency to reduce the excretion of albumin in the urine.

4. The method of claim 1 wherein, as a result of inflammatory intestinal pathology, an insufficiently functioning membrane of the intestine results in leakage of proteinic components into the lumen of the intestine, and wherein said oligosaccharide is administered in sufficient quantity and frequency to reduce said leakage into the lumen.

5. The method of claim 1 wherein, as a result of an inflammatory condition, an insufficiently functioning epithelial barrier results in leakage of proteinic components into the bladder, and wherein said oligosaccharide is administered in sufficient quantity and frequency to reduce said leakage into the bladder.

6. The method of claim 1 wherein, as a result of asthma, membranes of the lung perform insufficiently, and wherein said oligosaccharide is administered in sufficient quantity and frequency to reduce said leakage into the lung.

7. The method of claim 1 wherein the administration of said oligosaccharide is achieved by intravenous injection.

8. The method of claim 1 wherein the administration of said oligosaccharide is achieved by subcutaneous delivery.

9. The method of claim 1 wherein the administration of said oligosaccharide is achieved by intraperitoneal delivery.

10. The method of claim 1 wherein the administration of said oligosaccharide is achieved by inhalation into pulmonary proximity.

11. The method of claim 4 which comprises rectal delivery of a solution comprising said oligosaccharide in a physiologically acceptable solvent.

12. The method of claim 5 which comprises retrograde irrigation of the bladder with said oligosaccharide in a physiologically acceptable solvent.

13. The method of claim 6 which comprises preparing a nebulized solution of said oligosaccharide in a physiologically acceptable solvent; and delivering said solution by inhalation.

14. The method as claimed in claim 1 wherein said oligosaccharide is combined with at least one physiologically acceptable carrier.

15. The method as claimed in claim 14 wherein said carrier is a solvent for said oligosaccharide.

16. The method as claimed in claim 14 wherein said carrier is a biodegradable solid.

17. The method of claim 14 wherein said carrier also comprises a non-toxic, basic amino acid or organic diamine.

* * * * *